(12) United States Patent
Aberg et al.

(10) Patent No.: US 6,413,987 B1
(45) Date of Patent: Jul. 2, 2002

(54) DERMAL ANESTHETIC AGENTS

(75) Inventors: A. K. Gunnar Aberg, Sarasota, FL (US); George E. Wright; Jan L. Chen, both of Worcester, MA (US)

(73) Assignee: Bridge Pharma, Inc., Sarasota, FL (US)

( * ) Notice: Subject to any disclaimer, the term of this patent is extended or adjusted under 35 U.S.C. 154(b) by 0 days.

(21) Appl. No.: 09/588,582

(22) Filed: Jun. 6, 2000

Related U.S. Application Data

(60) Provisional application No. 60/138,353, filed on Jun. 10, 1999, and provisional application No. 60/179,267, filed on Jan. 31, 2000.

(51) Int. Cl.$^7$ .................. A61K 31/445; C07D 211/06
(52) U.S. Cl. ................ 514/319; 514/235.5; 514/239.5; 514/255; 514/318; 514/357; 514/422; 514/428; 514/643; 514/656; 514/657; 514/817; 514/818; 544/121; 544/131; 544/165; 544/360; 544/398; 544/399; 544/402; 546/194; 546/205; 546/304; 546/312; 548/523; 548/568; 548/569; 548/578; 564/194; 564/367; 564/369
(58) Field of Search ............................ 514/235.5, 239.5, 514/255, 318, 319, 357, 422, 428, 643, 656, 657, 817, 818; 544/124, 131, 165, 360, 398, 399, 402; 546/194, 205, 304, 312; 548/523, 568, 569, 578; 564/194, 367, 369

(56) References Cited

U.S. PATENT DOCUMENTS

| 3,923,813 A | 12/1975 | Vanhoof et al. ............. 546/205 |
| 3,923,815 A | 12/1975 | Vanhoof et al. ............. 546/232 |
| 3,923,887 A | 12/1975 | Vanhoof et al. ............. 564/194 |

FOREIGN PATENT DOCUMENTS

| GB | 1321424 | * | 6/1973 |

OTHER PUBLICATIONS

Dale et al. "Local anesthetic activity and toxicity of several esters of . . . " CA 48:8416 (1953).*

* cited by examiner

*Primary Examiner*—Ceila Chang
(74) *Attorney, Agent, or Firm*—Nields & Lemack

(57) ABSTRACT

The present invention relates to new aminoindane piperidine compounds, the method of using aminoindane compounds as local anesthetics, said compounds having particularly valuable properties as dermal and topical anesthetics in mammals, including man, as well as compositions containing said compounds.

18 Claims, No Drawings

DERMAL ANESTHETIC AGENTS

This application claims benefit to U.S. provisional application Ser. No. 60/138,353, filed Jun. 10, 1999, which claims benefit of U.S. provisional application Ser. No. 60/179,267, filed Jan. 31, 2000.

TECHNICAL FIELD

This invention relates to new chemical entities of the General Formula 1 as shown below, composition containing said chemical entities and to methods of using said chemical entities for the prevention and treatment of pain.

(Formula 1)

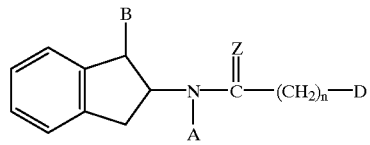

wherein n is equal to 1,2 or 3, A represents an aromatic substituent such as phenyl or a substituted phenyl, Z represents two hydrogen atoms or an oxygen atom, the $(CH_2)_n$ group having a straight or branched chain, B represents hydrogen, an alkoxy radical containing 1 to 3 carbon atoms or a group of the formula

in which $R_1$ and $R_2$ may independently be selected from the group consisting of methoxy, ethoxy, a lower alkyl or hydroxyalkyl radical containing 1 to 3 carbon atoms, D represents a group of the formula

in which $R_3$ represents hydrogen, a lower alkyl or hydroxyalkyl radical containing 1 to 3 carbon atoms, $R_4$ represents a lower alkyl or hydroxyalkyl radical containing 1 to 3 carbon atoms or a lower alkenyl or alkynyl radical containing 2 or 3 carbon atoms, whereby $R_1$ and $R_2$ may be identical or different and may also form together with the adjacent nitrogen atom a nitrogeous heterocyclic ring selected from the group consisting of piperidino, pyrrolidino, morpholino and piperazino rings. D may also represent a piperidine group, where the nitrogen substituent is selected from the group consisting of hydrogen, methyl, ethyl, propyl, butyl, hydroxyethyl, hydroxypropyl or hydroxybutyl and where the piperidine nucleus is attached at 2-, 3- or 4-position.

The chemical compounds of this invention have pharmacological properties that render said compounds to be useful in preventing and treating pain. The compounds can also be used to treat conditions, comprising convulsions, hiccup and cardiac arrhythmias and can be used to inhibit sodium and potassium ion fluxes over cell membranes in the body.

Prevention and treatment of pain using the compounds of this invention may be achieved by applying compositions containing said chemical entities on the skin or by applying compositions containing said chemical entities on mucosal membranes or by injecting solutions of said chemical entities to infiltrate biological tissues with said solutions or by injecting solutions of said chemical entities in the anatomical vicinity of nerves, thereby allowing said chemical entities to penetrate the biological tissues and cause dermal anesthesia, topical anesthesia, infiltration anesthesia or nerve blocks.

The invention also refers to compositions, containing at least one of said chemical entities and combinations of the present chemical entities with various other chemical entities and with various penetration promoting devices.

BACKGROUND OF THE INVENTION

Membrane stabilizing agents, such as lidocaine, prilocaine, mepivacaine and bupivacaine, have been shown to possess local anesthetic effects and are widely used for infiltration anesthesia and for inducing nerve blocks. These compounds have limited use as dermal anesthetics since they have to be given in high concentrations, which increases the risk of tissue irritation and tissue damage. Other compounds, such as tetracaine, are better suited for dermal anesthesia since they may better penetrate through the tissues. However, tetracaine and similar drugs are esters and are known to cause tissue irritation and to be unstable in the human body where practically all tissues contain esterases.

Objectives of the present invention are to obtain compounds that are potent membrane stabilizing agents with a prolonged effect as local anesthetics and topical anesthetics and dermal anesthetics and that have beneficial penetration properties and are able to penetrate the ocular tissues as well as mucosal tissues, including rectal tissues, and also penetrate through human skin after topical dermal application. Thus, the compounds of the invention will assure short onset time and long duration of local anesthesia, topical anesthesia and dermal anesthesia.

It is also an objective of the present invention to provide a method for local, topical and dermal anesthesia which is safe, effective, and has a minimum of side effects.

The mechanism of action of membrane stabilizing agents, when used as local anesthetic or topical anesthetic drugs, is to inactivate ion channels in nerves and thereby inhibit neuronal impulse conduction. To do this, the membrane stabilizing compound needs to overcome the local penetration barriers and reach the nerve structure in a concentration that is high enough to achieve the therapeutic objective. The compounds of the present invention have the ability to effectively overcome such tissue penetration barriers.

The term topical anesthesia is in this document defined as local anesthesia of mucosal membranes, such as for examples those of the eye, the ear, the mouth, the nose, the rectal area and the urogenital tract. The term dermal anesthesia is in this document defined as local anesthesia of the skin. Infiltration anesthesia and nerve blocks of afferent or efferent nerves are in this document called local anesthesia.

SUMMARY OF THE INVENTION

The present invention relates to new nerve membrane stabilizing compounds as described above and to methods of inducing local, topical or dermal anesthesia, by administering a composition containing at least one such chemical entity that has such penetration properties that it in a short period of time can reach the site of action on the nerve ending or a nerve in a concentration that will block the initiation or conduction of nerve impulses. It has been found that compositions containing at least one of the compounds of the present invention are particularly useful for ocular and dermal anesthesia and for other forms of local anesthesia, such as for example infiltration anesthesia and nerve blocks. The compounds of the present invention are useful for the prevention of pain in connection with inserts of injection needle, surgical procedures and for the treatment of pain in connection with the above mentioned medical procedures, insect bites, sunburn, and for the treatment of shingles and urogenital pain, including hemorrhoids.

Thus, the present invention provides effective methods for treating humans and animals with topical, dermal and local anesthetic compositions, while reducing undesirable side effects, for example local burning and itching and particularly tissue toxicity resulting in necrosis.

DETAILED DESCRIPTION OF THE INVENTION

The objective of the present invention is to obtain compounds that have topical, dermal and local anesthetic effects and that can be administered either by injection or by topical or dermal application and that offer a short onset time and a long lasting effect.

It has now been found that compounds of the formulas below possess such properties.

Compounds of the invention are those of the general Formula 1

(Formula 1)

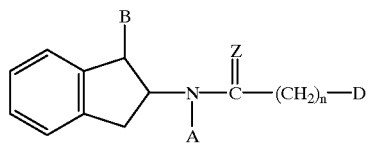

wherein n is equal to 1,2 or 3, A represents an aromatic substituent much as phenyl or substituted phenyl, Z represents two hydrogen atoms or an oxygen atom, the $(CH_2)_n$ group having a straight or branched chain, B represents hydrogen, an alkoxy radical containing 1 to 3 carbon atoms or a group of the formula

in which $R_1$ and $R_2$ may independently be selected from the group consisting of methoxy, ethoxy, a lower alkyl or hydroxyalkyl radical containing 1 to 3 carbon atoms, whereby $R_1$ may also represent hydrogen, A is a 2-pyridyl radical, an unsubstituted phenyl radical or a phenyl radical substituted by at least one substituent in the ortho, meta and/or para position D represents a group of the formula

in which $R_3$ represents hydrogen, a lower alkyl or hydroxyalkyl radical containing 1 to 3 carbon atoms, $R_4$ represents a lower alkyl or hydroxyalkyl radical containing 1 to 3 carbon atoms or a lower alkenyl or alkynyl radical containing 2 or 3 carbon atoms, whereby $R_3$ and $R_4$ may be identical or different and may also form together with the adjacent nitrogen atom a nitrogeous heterocyclic ring selected from the group consisting of piperidino, pyrrolidino, morpholino and piperazino rings. D may also represent a piperidine group, where the nitrogen substituent E is selected from the group comprising hydrogen, methyl, ethyl, propyl, butyl, hydroxyethyl, hydroxypropyl or hydroxybutyl and where the piperidine nucleus is attached at 2-, 3- or 4-position.

(Formula 2)

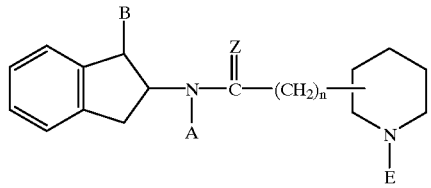

Compounds of Formula 2 above may be prepared according to the following methods:

a) by reacting a compound of Formula 3

(Formula 3)

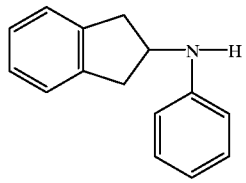

with a compound of the formula 4, (Formula 4)

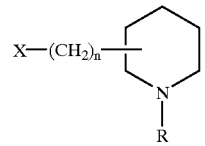

wherein R and n have the meanings given above except that R may not be hydrogen, and X is a halogen (Cl, Br or I) or a reactive esterified hydroxy group, to form a compound of formula 5; and b) by hydrogenating a compound of formula 2, wherein E is a residue removable by means of reduction, and n has the meaning given above, to give a compound of the formula 5 wherein E is not hydrogen;

c) by hydrolyzing a compound of the formula 5, (Formula 5)

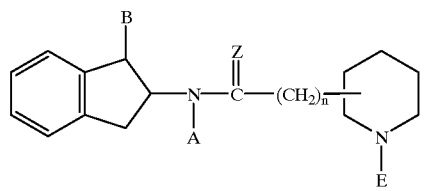

wherein E is a residue removable by means of hydrolysis, and n has the meaning given above, to form a compound of formula 5, wherein R is hydrogen.

The reactions are carried out in an inert organic solvent such as benzene or toluene in the presence of a strong base such as sodium amide or sodium hydride.

In the method a) above X may be halogen (Cl, Br or I) or a reactive, esterified hydroxy group, that is a hydroxy group esterified with a strong, organic acid such as trifluoromethanesulfonic acid, trifluoroacetic acid, trichloroacetic acid, benzenesulfonic acid, 4-bromobenzenesulfonic acid or 4-toluenesulfonic acid.

In method c) above, a residue removable by means of hydrolysis may be e.g. an acyl residue, which, when present, is a functionally varied carboxy group, e.g. oxycarbonyl or alkoxycarbonyl residues, such as tert-butoxycarbonyl residue, or ethoxycarbonyl residue; an aralkoxycarbonyl residue such as phenyl substituted lower alkoxycarbonyl residue, e.g. a carbobenzyloxy residue; a halogencarbonyl residue, e.g. a chlorocarbonyl residue; an arylsulphonyl residue such as toluenesulphonyl or bromobenzenesulphonyl residues; a halogenated, e.g. fluorinated, lower alkanoyl residue as formyl-, acetyl- or trifluoroacetyl residue; or a benzyl residue, a cyano group, or a silyl residue, such as trimethylsilyl residue.

The hydrolysis is carried out in a known way, e.g. in the presence of a hydrolyzing agent, e.g. in the presence of an acidic agent such as diluted mineral acid, e.g. sulphuric acid or hydrohalogen acid; or in the presence of a basic agent such as an alkali metal hydroxide, e.g. sodium hydroxide. Oxycarbonyl residues, arylsulphonyl residues and cyano groups may be split off in a suitable way by means of acidic agents such as hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "cyanogen bromide method" (v. Braun). Furthermore, a tert-butoxycarbonyl residue may be split off under anhydrous conditions by means of treatment with a suitable acid, as trifluoroacetic acid.

In method b) above, a residue removable by means of reduction is e.g. an alpha-arylalkyl residue, such as a benzyl residue, or an alpha-aralkoxycarbonyl residue such as a benzyloxycarbonyl residue, which in a known way may be split off by means of a hydrogenolysis especially by catalytically activated hydrogen, as by hydrogen in the presence of hydrogenating catalysts, e.g. Raney-nickel or palladium on carbon. Other residues removable by means of reduction are 2-halogenalkoxycarbonyl residues as 2,2,2-trichloroethoxycarbonyl residues or 2-iodoethoxy- or 2,2,2-tribromoethoxycarbonyl residues, which may be split off in a known way, suitably by means of a metallic reduction (so-called nascent hydrogen). Nascent hydrogen may be obtained by the action of metal, or metal alloy as amalgam, on compounds which give hydrogen, such as carboxyacids, alcohols or water, whereby especially zinc or zink alloys together with acetic acid may be used. Splitting off of 2-halogenalkoxy-carbonyl residues may likewise take place using chromium or chromium (II) compounds as chromium (II) chloride or chromium (II) acetate.

A residue removable by reduction may also be such an arylsulphonyl group as a toluenesulphonyl group, which in a known way may be split off by reduction using nascent hydrogen, i.e. by means of an alkalimetal, such as lithium or sodium, in liquid ammonia and suitably may be split off from a nitrogen atom. When a residue is removed by reduction, one must take care to avoid reduction of other reducible groups in the molecule.

The nitrogen atom in the piperidine nucleus may also be substituted with a residue removable by means of ammonolysis, pyrolysis and fermentation, to form a compound of the Formula I, wherein R is hydrogen.

Residues splittable by ammonolysis are especially the halogen-carbonyl residues, as the chlorocarbonyl residue. The ammonolysis may be carried out in a common way, e.g. by means of an amine containing at least one hydrogen atom bounded to the nitrogen atom, as a mono-or diloweralkylamine, e.g. methylamine or dimethylamine, or especially ammonia, preferably at an elevated temperature. Instead of ammonia one may use an agent which gives ammonia as hexamethylenetetraamine.

Residues splittable by means of pyrolysis, especially residues splitable from the nitrogen atom, are in occurring cases substituted, preferably unsubstituted, carbamoyl groups. Suitable substituents are e.g. loweralkyl, or aryllow-eralkyl as methyl or benzyl or aryl, as phenyl. The pyrolysis is carried out in a common way, whereby one must take care to avoid pyrolysis of other thermically susceptible groups.

Residues splittable by means of fermentation, especially residues splitable from the nitrogen atom are in occurring cases substituted, however preferably unsubstituted carbamoyl groups. Suitable substituents are e.g. loweralkyl or arylloweralkyl, as methyl or benzyl, or aryl as phenyl. The fermentation is carried out in a common way, e.g. by means of the enzyme urease or soybean extract at about 20° C. or at a slightly elevated temperature.

The piperidine-containing compounds of the invention are those of the general formula 2 wherein E is selected from the group consisting of hydrogen, methyl, ethyl, propyl, butyl, hydroxyethyl, hydroxypropyl or hydroxybutyl and where A, B, Z and n are as stated above. Starting material and compounds of formula 6 above have been prepared.

(Formula 6)

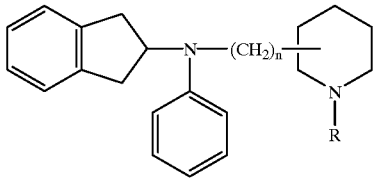

Examples of Synthetic Routes:

EXAMPLE 1

Synthesis of Starting Material (SM)

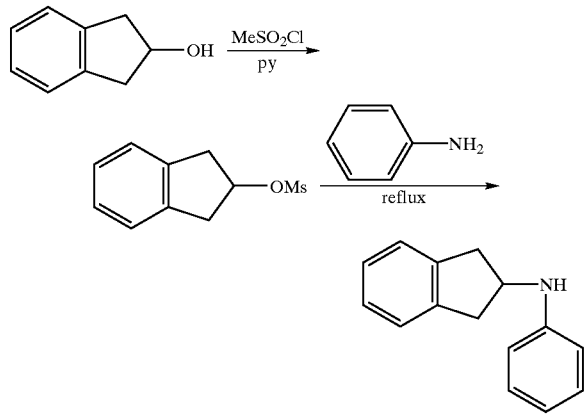

Synthesis of 1-benzyl-2-chloromethylpiperidine.

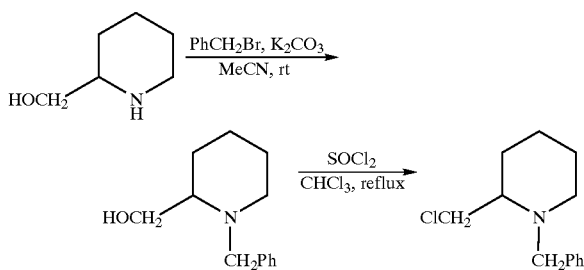

A mixture of piperidinemethanol (24.5 g, 0.21 mol), benzyl bromide (27.5 ml, 0.23 mol), potassium carbonate (58 g, 0.42 mol) in acetonitrile (250 ml) was stirred at room temperature overnight. After concentration in vacuo, the residue was treated with water and extracted with ethyl acetate. The organic layer was dried over sodium sulfate, and the filtrate was evaporated. The residual oil was dried under high vacuum (43 g alcohol). Thionyl chloride (16 ml) was added dropwise to a solution of the above alcohol (43 g) in chloroform (70 ml) at room temperature. After stirring at reflux for 3 h, the solution was cooled and concentrated in vacuo, and the residue was treated with water and extracted with methylene chloride. The organic layer was washed with aqueous sodium bicarbonate and brine, and dried overnight over sodium sulfate. The filtrate was evaporated, and the residue was purified on silica gel column. Elution with ethyl acetate: petroleum ether (1:9) gave 1-benzyl-2-chloromethylpiperidine (44 g) as oil.

EXAMPLE 2

2-[(N-Phenyl-N-2-indanyl)aminomethyl]piperidine Hydrochloride (TAC 28)

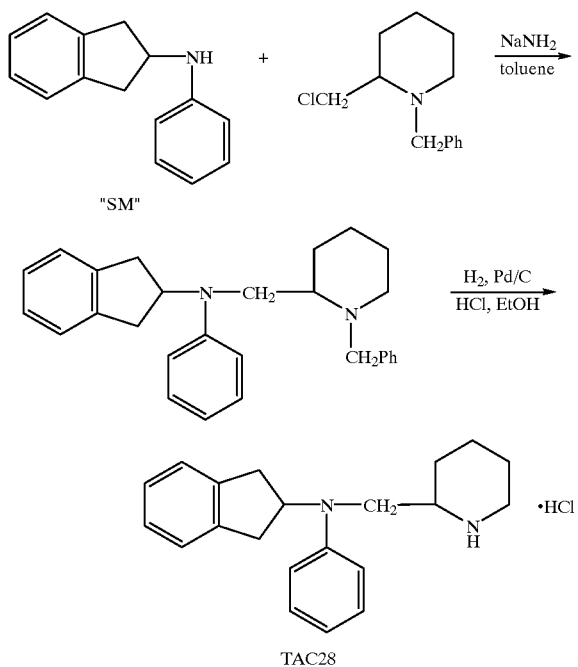

N-Phenyl-2-aminoindane, i.e. SM, (13.2 g, 67 mmol) was dissolved in dry toluene (220 ml), and sodium amide (4.5 g, 115 mmol) was added to the stirred solution at room temperature. After 3 h, 1-benzyl-2-chloromethylpiperidine (15 g, 63 mmol) was added and the mixture was stirred at reflux for 20 h. The mixture was poured into water and extracted with diethyl ether. The ether layer was washed with water and brine and dried over sodium sulfate. After evaporation of solvent the residue was purified on a silica gel column with ethyl acetate:petroleum ether (1:9) as eluent. The product as the free base (21 g, 79%) was isolated as an oil.

A solution of free base (19 g) in ethanol (300 ml) was acidified to pH 4 with hydrochloric acid in methanol. The mixture was hydrogenated at room temperature at 50 psi using Pd/C (10%, 0,5 g) as catalyst. The mixture was filtrated and concentrated, and the residue was crystallized from acetonitrile to give 10.2 g (56%) of TAC 28 as the hydrochloride.

EXAMPLE 3

1-Butyl-2-[(N-phenyl-N-2-indanyl)aminomethyl] piperidine HCl (TAC 50)

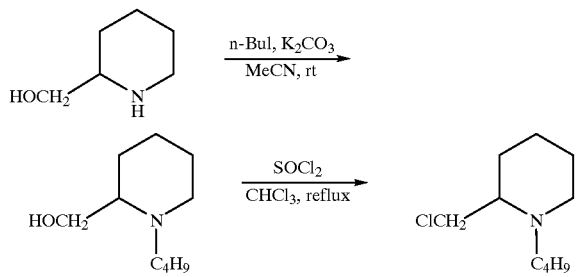

n-Butyl iodide (9.2 g, 50 mmol) was added to a mixture of SM (5.8 g, 50 mmol) and potassium carbonate (7.0 g) in acetonitrile (200 ml). After stirring at the overnight, the mixture was concentrated in vacuo, and the residue was treated with water and extracted with ethyl acetate (1:1) as eluent to give 1-butyl-3-piperidinemethanol (7.3 g, 85%)as an oil.

Thionyl chloride (3.2 ml, 42 mmol) was added dropwise to a stirred solution of this intermediate (7.3 g, 42 mmol) in chloroform (20 ml). After stirring at reflux for 3 h the cooled solution was concentrated in vacuo, and the residue was treated with aqueous sodium bicarbonate and extracted with methylene chloride. The organic layer was washed wit aq. sodium bicarbonate and brine, dried over sodium sulfate, and the residue purified on a silica gel column. The yield of 1-butyl-2-(chloromethyl)piperidine was 3.8 g (48%).

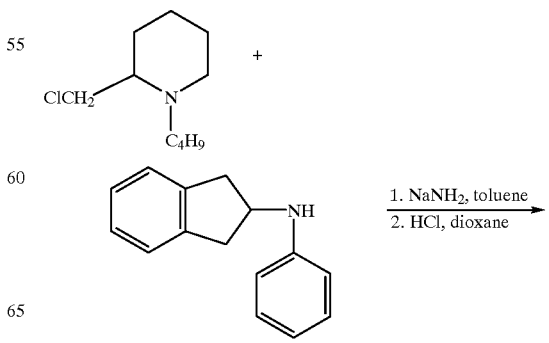

-continued

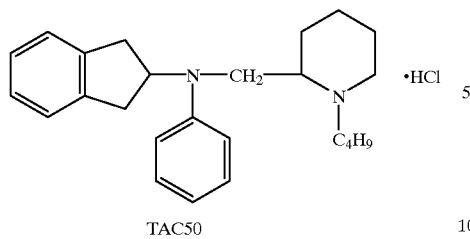

TAC50

Reaction of this intermediate (3.8 g, 20 mmol) with SM (4.4 g, 22mmol) and sodium amide (1.5 g, 38 mmol) in toluene (70 ml), as described above in b., gave 4.6 g of the free base i-butyl-2-[(N-phenyl-N-2-indanyl) aminomethyl]piperidine. The compound was converted to the hydrochloride (5.1 g).

EXAMPLE 4

1-Methyl-2-[(N-phenyl-N-2-indanyl)aminomethyl] piperidine HCl (TAC 29)

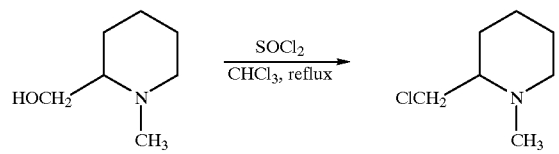

Treatment of 1-methyl-2-piperidinemethanol (12.9 g, 0.1 mol) with thionyl chloride (7.6 ml) in chloroform (40 ml), as described in example 3, gave 1-methyl-2-(chloromethyl) piperidine (5.0 g, 34%).

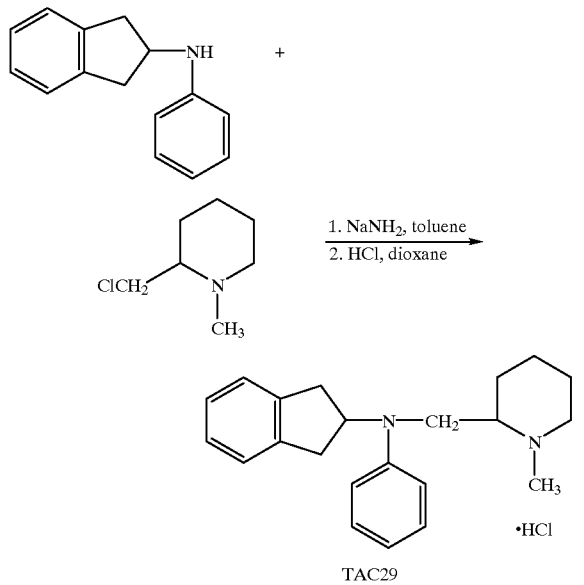

TAC29

Reaction of this intermediate (5.0 g, 34 mmol) with SM (7.8 g, 37 mmol) and sodium amide (2.5 g, 62 mmol) in toluene (120 ml), as described above in EXAMPLE 3, gave 9.9 g (91%) of the free base 1-methyl-2-[(N-phenyl-N-2-indanyl)aminomethyl]piperidine Treatment with hydrogen chloride in dioxane gave colorless crystals of the hydrochloride salt, 11.0 g.

EXAMPLE 5

1-(2-Hydroxyethyl)2-[(N-phenyl-N-indanyl) aminomethyl]piperidine HCl. (TAC 31)

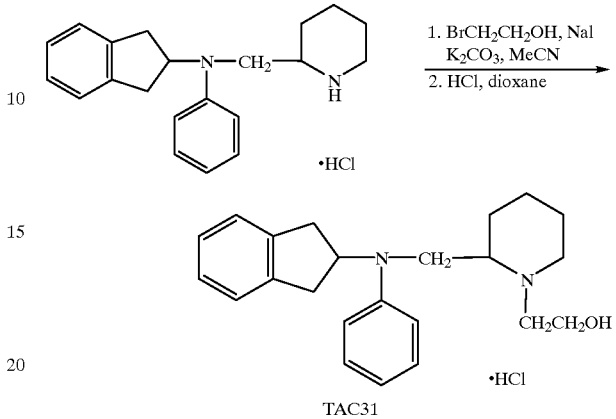

TAC31

2-Bromoethanol (2.8 g, 22.5 mmol) was added to a mixture of TAC 28 (5.1 g, 15 mmol), sodium iodide (1 g, 6 mmol) and potassium carbonate (15 g) in acetonitrile (100 ml). After stirring for 3 days at room temperature, the mixture was concentrated in vacuo, and the residue was treated with water, extracted with ethyl acetate, and the residue purified on a silica gel column. Elution with ethyl acetate:methanol:triethylamine (9:1:0.3) gave the product free base (4.9 g, 93%) as an oil. Treatment of the free base with hydrogen chloride in dioxane gave 5.4 g of TAC 31 hydrochloride as colorless crystals.

EXAMPLE 6

Starting Material 1-Benzyl-2-(2-chloroethyl) piperidine

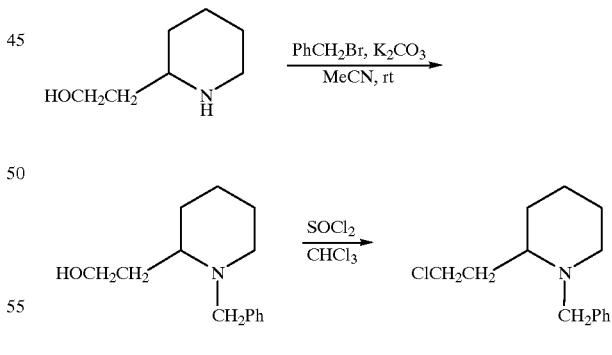

2-Piperidineethanol (25.8 g, 0.2 mol), benzyl bromide (26.2 ml) and potassium carbonate (55.3 g) in acetonitrile (250 ml), as described above, gave 1-benzyl-2-piperidineethanol (43.8 g, 100%).

Treatment of this intermediate with thionyl chloride (15.3 ml, 0.2 mol) in chloroform (150 ml), as described in Example 2 above, gave 1-benzyl-2-(2-chloroethyl) piperidine (36.7 g, 75%) as an oil.

EXAMPLE 7

2-[2-(N-Phenyl-N-2-indanyl)aminoethyl]piperidine HCl (TAC 34)

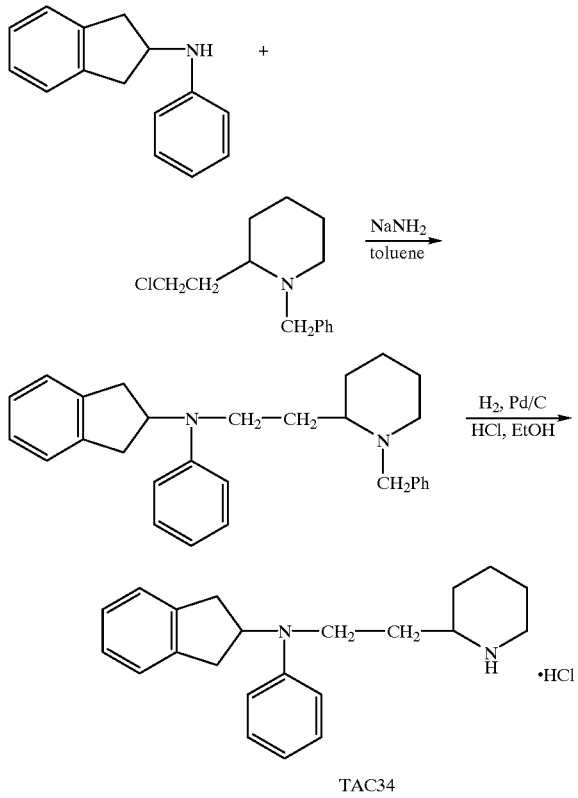

TAC34

1-Benzyl-2-(2-chloroethyl)piperidine (36.7 g, 0.15 mol), SM (34.3 g, 0.16 mmol) and sodium amide (11 g, 0.28 mol) in toluene (500 ml), as described in Example 3 above, gave 27 g (44 %) of the free base 2-[2-(N-phenyl-N-2-indanyl)aminoethyl]piperidine.

Hydrogenation of the free base, as described in Example above, gave 19.5 g (55%) of TAC 34 as the hydrochloride.

EXAMPLE 8

1-Butyl-2-[(N-phenyl-N-2-indanyl)aminoethyl]piperidine HCl (TAC 51)

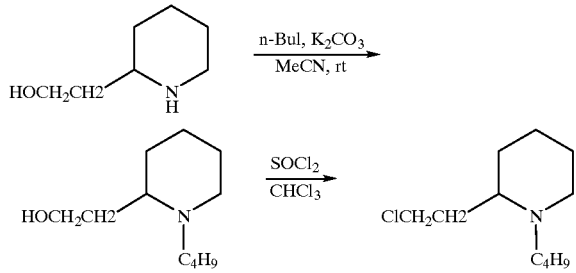

2-Piperidineethanol (15 g, 0.12 mol), n-butyl iodide (23.5 g, 0.13 mol) and potassium carbonate (32.1 g, 0.23 mol) in actonitrile (250 ml), as described in example 3 above, gave 1-butyl-2-piperidineethanol (16.2 g, 75%).

This intermediate and thionyl chloride (6.7 ml) in chloroform (250 ml), as described in example 3 above, gave 1-butyl-2-(2-chloroethyl)piperidine (11.9 g, 68%).

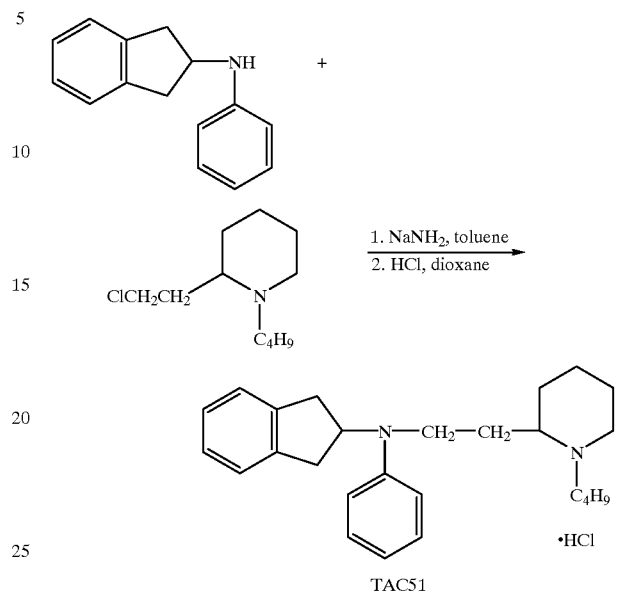

TAC51

1-Butyl-2-(2-chloroethyl)piperidine (10.7 g, 53 mmol), SM (12.1 g, 58 mmol) and sodium amide (3.8 g, 96 mmol) in to;uene (250 ml), as described in 2. c. above, gave the free base 1-butyl-2-[(N-phenyl-N-2-andanyl)aminoethyl]piperidine. Treatment of the free base with hydrogen chloride in dioxane, as described in 2c. above, gave TAC 51 (7.6 g, 35%) as colorless crystals.

EXAMPLE 9

1-(2-Hydroxyethyl)-2-[2-(N-phenyl-N-2-indanyl)aminoethyl]piperidine Hydrochloride (TAC 40)

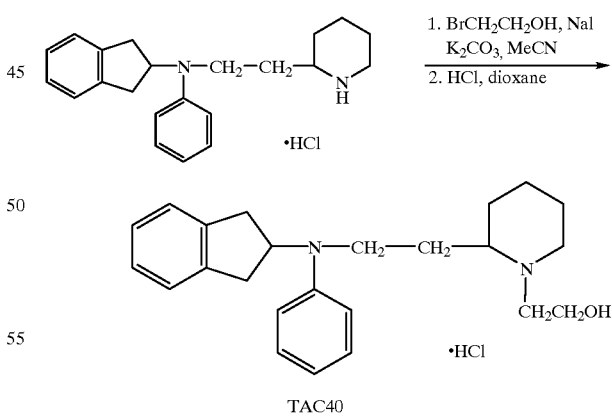

TAC40

TAC 34 (10 g, 28 mmol), 2-bromoethanol (3.9 g), sodium iodide (1.7 g) and potassium carbonate (11.6 g) in acetonitrile (200 ml), as described in Example 3 above, gave 4.0 g (40%) of the free base 1-(2-hydroxyethyl)-2-[2-(N-phenyl-N-2-indanyl)aminoethyl]piperidine. Treatment of the free base with hydrogen chloride in dioxane gave 4.2 g of the hydrochloride of TAC40 as colorless crystals.

Thus the piperidine-containing compounds of the present invention can be synthesized according to the following methods:

a) by reacting a compound of formula 7

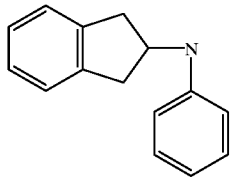

(Formula 7)

with a compound of the formula 8,

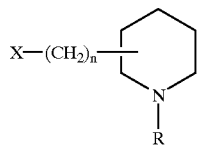

(Formula 8)

wherein R and n have the meanings given above except that R may not be hydrogen, and X is a halogen or a reactive esterified hydroxy group, to form a compound of formula 1; and b) by hydrogenating a compound of formula 9,

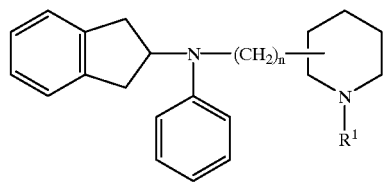

(Formula 9)

wherein $R^1$ is a residue removable by means of reduction, and n has the meaning given above, to give a compound of the formula 1 above wherein R is hydrogen; and c) by hydrolyzing a compound of the formula 10, wherein $R^2$ is a residue removable by means of hydrolysis, and n has the meaning given above, to form a compound of formula 1, wherein R is hydrogen.

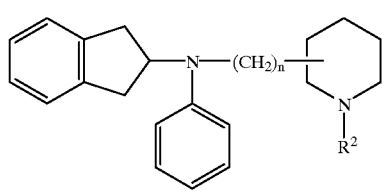

(Formula 10)

The reactions are carried out in an inert organic solvent such as benzene or toluene in the presence of a strong base such as sodium amide or sodium hydride.

In the method a) above X may be a halogen such as Cl, Br or I, or a reactive, esterified hydroxy group, that is, a hydroxy group esterified with a strong organic acid, such as methanesulfonic acid, trifluoromethanesulfonic acid, benzenesulfonic acid, 4-bromobenzene-sulfonic acid, or 4-toluenesulfonic acid.

In method c) above, a residue removable by means of hydrolysis may be e.g. an acyl residue, which, when present, is a functionally varied carboxy group, e.g. oxycarbonyl or alkoxycarbonyl residues, such as tert.butoxycarbonyl residue, or ethoxycarbonyl residue; an aralkoxycarbonyl residue such as phenyl substituted lower alkoxycarbonyl residue, e.g. a carbobenzyloxy residue; a halogencarbonyl residue, e.g. a chlorocarbonyl residue; an arylsulfonyl residue such as toluenesulfonyl or bromobenzenesulfonyl residues; a halogenated, e.g. fluorinated, lower alkanoyl residue as formyl-, acetyl- or trifluoroacetyl residue; or a benzyl residue, a cyano group, or a silyl residue, such as trimethylsilyl residue. the hydrolysis is carried out in a known way, e.g. in the presence of a hydrolyzing agent, e.g. in the presence of an acidic agent such as diluted mineral acid, e.g. sulphuric acid or hydrohalogen acid; or in the presence of a basic agent such as an alkali metal hydroxide, e.g. sodium hydroxide. Oxycarbonyl residues, arylsulfonyl residues and cyano groups may be split off in a suitable way by means of acidic agents such as hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "cyanogen bromide method" (v. Braun). Furthermore, a tert-butoxycarbonyl residue may be split off under anhydrous conditions by means of treatment with a suitable acid, as trifluoroacetic acid.

In method b) above, a residue removable by means of reduction is e.g. an alpha-arylalkyl residue, such as a benzyl residue, or an alpha-aralkoxycarbonyl residue such as a benzyloxycarbonyl residue, which in a known way may be split off by means of a hydrogenolysis especially by catalytically activated hydrogen, as by hydrogen in the presence of hydrogenating catalysts, e.g. Raney-nickel or palladium on carbon. Other residues removable by means of reduction are 2-halogenalkoxycarbonyl residues as 2,2,2-trichloroethoxycarbonyl residues or 2-iodoethoxy- or 2,2,2-tribromoethoxycarbonyl residues, which may be split off in a known way, suitably by means of a metallic reduction (so-called nascerating hydrogen). Nascerating hydrogen may be obtained by the action of metal, or metal alloy as amalgam, on compounds which give hydrogen, such as carboxyacids, alcohols or water, whereby especially zinc or zinc alloys together with acetic acid may be used. Splitting off of 2-halogenalkoxycarbonyl residues may likewise take place using chromium or chromium (II) compounds as chromium (II) chloride or chromium (II) acetate.

A residue removable by reduction may also be such an arylsulfonyl group as a toluenesulfonyl group, which in a known way may be split off by reduction using nascerating hydrogen, i.e. by means of an alkali metal, such as lithium or sodium, in liquid ammonia and suitably may be split off from a nitrogen atom. When a residue is removed by reduction, one must take care to avoid reduction of other reducible groups in the molecule.

The nitrogen atom in the piperidine nucleus may also be substituted with a residue removable by means of ammonolysis, pyrolysis and fermentation, to form a compound of the formula I, wherein R is hydrogen.

Residues splittable by ammonolysis are especially the halogeno-carbonyl residues, as the chlorocarbonyl residue. The ammonolysis may be carried out in a common way, e.g. by means of an amine containing at least one hydrogen atom bounded to the nitrogen atom, as a mono- or di-loweralkylamine, e.g. methylamine or dimethylamine, or especially ammonia, preferably at an elevated temperature. Instead of ammonia one may use an agent which gives ammonia as hexamethylenetetraamine.

Residues splittable by means of pyrolysis, especially residues splittable from the nitrogen atom, are in occurring cases substituted, preferably unsubstituted, carbamoyl groups. Suitable substituents are e.g. loweralkyl, or aryllloweralkyl as methyl or benzyl or aryl, as phenyl. The pyrolysis is carried out in a common way, whereby one must take care to avoid pyrolysis of other thermically susceptible groups.

Residues splitable by means of fermentation, especially residues splittable from the nitrogen atom are in occurring cases substituted, however preferably unsubstituted carbamoyl groups. Suitable substituents are e.g. loweralkyl or arylloweralkyl, as methyl or benzyl, or aryl as phenyl. The fermentation is carried out in a common way, e.g. by means of the enzyme urease or soy bean extract at about 20° C. or at a slightly elevated temperature.

Depending on the process conditions and the starting materials, the end product is obtained either as the free base or as the acid addition salt, both of which are included within the scope of the invention. Thus, basic, neutral or mixed salts may be obtained, as well as hemi-, mono-, sesqui-, or polyhydrates. The acid addition salts of the new compounds may be transformed in a manner known per se into free base using basic agents such as alkali or by ion exchange. On the other hand, the free bases obtained may form salts with organic or inorganic acids. In the preparation of acid addition salts preferably such acids are used which form suitable therapeutically acceptable salts. Such acids include hydrohalogen acids, sulfuric, phosphoric, nitric, and perchloric acids; aliphatic, alicyclic, aromatic, heterocyclic carboxy or sulfonic acids, such as acetic, formic, propionic, succinic, glycolic, lactic, malic, tartaric, citric, ascorbic, maleic, hydroxymaleic, pyruvic, phenylacetic, benzoic, p-aminobenzoic, anthranilic, p-hydroxybenzoic, salicylic or p-aminosalicylic acid, embonic, methanesulfonic, ethane sulfonic, hydroxyethanesulphonc, ethylenesulphonic, halogenbenzenesulphonic, toluenesulfonic, naphtylsulfonic, or sulfanilic acids; methionine, tryptophane, lysine or arginine.

These and other salts of the new compounds, as e.g. picrates, may serve as purifying agents of the free bases obtained. Salts of the bases may be formed, separated from the solution, and then the free base can be recovered from the new salt solution in a purer state. Because of the relationship between the new compounds in free base form and their salts, it will be understood that the corresponding salts are included within the scope of the invention.

The starting materials are known or may, if they should be new, be obtained according to processes known per se.

In clinical use the compounds of the invention are administered by injection, transdermally, topically or epidermally in the form of a pharmaceutical preparation which contains at least one compound of the invention either as a free base or as a pharmaceutically acceptable, non-toxic acid addition salt, such as for example hydrochloride, lactate, acetate, sulfamate, in combination with a pharmaceutically acceptable carrier. Usually the amount of active compound is between 0.05 and 10% by weight of the preparation: between 0.05 and 2.5% by weight in preparations for ocular use, between 0.5 and 10% by weight in preparations for dermal anesthesia, between 0.5 and 5% by weight in preparations for non-ocular topical (ex. oral, nasal, rectal, urethral, vaginal, etc.) use, between 0.25 and 3% for injections and between 0.1 and 3% for infusions (ex. for epidural, spinal or regional anesthesia). In any case, the quantity of the drug to be administered will be determined on an individual basis, and will be based on the pharmacological potency of the drug, the route of administration and at least in part on consideration of the individual's size, the severity of the symptoms to be treated and the results sought. In general, quantities of a compound of the invention sufficient to eliminate the unwanted condition will be administered. The actual dosage (concentration and volume) and the number of administrations per day will depend on the pharmacokinetic properties of the drug and the mode of drug administrations, for example, by topical doses to the eye.

In the present method, the compounds of the invention can be administered topically to the eye, for example as solutions, suspensions or ointments. The ophthalmically compatible carrier which may be used in this invention comprises e.g. an aqueous solution, such as saline solution, oil solution or ointments containing ophthalmically compatible preservatives, surfactants, buffers, and agents such as polymers to increase the viscosity. These compositions may also contain stabilizing agents, antibacterial agents, buffering agents and may be manufactured in different dosage units, suitable for ocular administration. Also drug inserts, either soluble or insoluble, may be used.

Solutions for injection or infusion may be prepared as aqueous solutions of a water soluble, pharmaceutically acceptable salt of the active compound, preferably in a concentration from 0.1 to 3.0%. These solutions may also contain stabilizing agents, antibacterial agents, buffering agents and may be manufactured in different dosage unit ampoules or bottles.

Dosage units for rectal administration may be prepared in the form of ointments or suppositories, which contain the active substance in a mixture with a neutral fat base, or they may be prepared in the form of gelatin-rectal capsules that contain the active compound in a mixture with for example a vegetable oil or paraffin oil. Ointments, suppositories or cremes containing at least one of the compounds of the invention are useful for the treatment of hemorrhoids and compounds of the invention having topical anesthetic effects in combination with vasoconstrictor effects are particularly useful for the treatment of hemorrhoids.

Dosage forms for dermal anesthesia may be prepared for example as a solution, ointment or cream. The dermal composition may also contain emulsifiers (e.g. polyoxyethylene fatty acid esters), thickening agents (e.g. carboxypolymethylene), pH-adjusting agents (e.g. sodium hydroxide), preservatives, penetration promoting agents (e.g. hydroxypolyethoxydodecane, DMSO, DMAC, etc). The dermal composition may contain one or more active compounds and the compounds may be prepared as bases or salts to facilitate dermal penetration. The composition may be applied to the skin under occlusive dressing or as a constituent of a dermal delivery system ("patch" etc.)

In the method of the present invention, the compounds of the invention can be administered together with one or more other compound(s). For example, injectable solutions may contain a vasoconstrictor (e.g. epinephrine or vasopressin); a solution for infusion or regional anesthesia may contain glucose or dextrose, a jelly for urogenital topical procedures may contain thickening agents (e.g. hydroxypropylmethylcellulose); a preparation for topical or dermal application may contain penetration promoting agents (e.g. hydroxypolyethoxydodecane, DMSO, DMAC); sprays for topical anesthesia of the mouth and oropharynx may contain saccharin and alcohol, ointments for accessible mucous membranes may contain a lubricant. The compounds of the invention can also be administered together with other membrane stabilizers (local anesthetics), for example to form eutectic mixtures.

Biological Testing

A. Topical Anesthetic Activity.

Aliquots (0.25 ml) of test solutions were applied into the conjunctival sac of conscious rabbits (either sex; 2–4 kg) and the eye-lids were kept closed for approximately 20 sec. The corneal reflex was checked before application of the test solution and every 5 min thereafter. To test the corneal reflex, the cornea was touched six times with a stalked elastic bristle. The duration of anesthesia was calculated as the period from the time-point when the animal did not feel any of the six touches by the am bristle to the time point when the animal again reacted to three of the six touches. To verify the reversibility of the topical anesthetic effect, the testing continued until the animal reacted to all six touches of the bristle for at least 15 minutes.

B. Dermal Anesthetic Activity.

Approximately 18–24 hours before each experiment, the skin on the back of male guinea pigs was shaved and depilated with a commercially available hair remover. The anesthetic action of each agent following dermal application was determined using a "pin-prick" method as described by Aberg (Acta Pharmacol Toxicol, 1972, 31: 273–286). Before and at various intervals after treatment, the area of the skin was tested for the presence or absence of a skin twitch in response to six standardized dermal probings with a pointed metal "algesimeter" at a predetermined maximum load of 10 grams. The average number of probings not producing a skin twitch response was designated as the "anesthetic score". In this system six responses to six stimuli represents "no anesthetic activity" and no response to six stimuli represents a "maximal anesthetic activity". In experiments on the dermal anesthetic activity, a single area of skin 1 inch square was marked off on the middle of the back of each animal. This area was covered by a 1 inch square, 16 layer thick gauze pad onto which was deposited 0.45 ml of a 10% solution of the test agent in water with DMSO. The gauze pad was covered with a 1.5 inch square sheet of Saran Wrap™ which was attached to the surrounding skin with tape. The entire area was then covered by wrapping an elastic bandage around the trunk of the animal. After a predetermined duration of treatment, the coverings were removed and the skin assessed for the presence of anesthesia as described above. Dermal anesthesia tests were performed at ten minute intervals to measure onset time and duration of dermal anesthetic activity; comparisons were made with reference compounds and vehicle. All test compounds were in the base form and dissolved in DMSO/water when tested for dermal anesthesia.

C. Local (infiltration) Anesthetic Activity.

Approximately 18–24 hours before each experiment, the skin on the back of male guinea pigs was shaved and depilated with a commercially available hair remover. The anesthetic action of each agent following intradermal injection was determined using a "pin-prick" method as described by Aberg (Acta Pharmacol Toxicol, 1972, 31: 273–286). Before and at various intervals after treatment, the area of the skin was tested for the presence or absence of a skin twitch in response to six standardized cutaneous probings with a pointed metal "algesimeter" at a predetermined maximum force of 20 grams. The average number of probings not producing a skin twitch response was designated as the "anesthetic score". In this system six responses to six stimuli represents "no anesthetic activity" and no response to six stimuli represents a "maximal anesthetic activity". In experiments with intradermal injections of agents, the backs of the guinea pigs are divided into four sections using a marking pen, and injections of 0.1 ml of 0.25%, 0.5% and 1.0% solutions of the test compounds in physiological saline, vehicle (physiological saline) and at least one reference compounds were made, one injection into each of the four defined areas.

All test compounds were in salt form (usually hydrochlorides) and dissolved in physiological saline when tested for infiltration anesthesia.

D. Acute Intravenous Toxicity in Mice.

Mice (males) of the NMRI strain, weighing 20 to 22 g were used after a stabilization period of at least ten days at the testing facility and at least one hour in the laboratory. Food but not water had been withheld from all animals for 16 hours before the test. The animals were again given free access to food starting two hours after the drug administration, that usually took place around 9:00 AM. All animals are observed daily for 7 days post dosing.

EQUIVALENTS

Those skilled in the art will recognize, or be able to ascertain, using no more than routine experimentation, many equivalents to the specific embodiments of the invention described herein. Thus, the piperidine moiety of Formula 2 may be substituted with an azabicyclo moiety that may also be attached in ortho, meta or para positions. The compounds of the present invention may be used also for other indications, such as for example to prevent or treat smooth muscle spasms, cardiac arrhythmias and hiccup. The use of a single isomer may have the advantage that side effects residing in the other isomer can be avoided. Thus nervous system side effects, such as for example effects on respiration and cardiovascular side effects, such as for example negative inotropic effects, negative chronotropic effects and negative dromotropic effects may be completely or partially avoided by using a single isomer. All equivalents are intended to be encompassed in the scope of the following claims.

We claim:

1. A compound having the formula

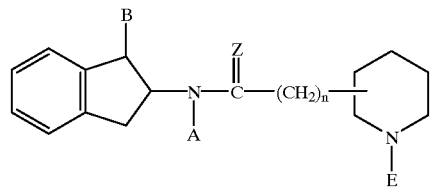

(Formula 1)

or an optically active isomer thereof, wherein n is equal to 1, 2, or 3, A represents an aromatic substituent such as phenyl or substituted phenyl, Z represents two hydrogen atoms or an oxygen atom, the $(CH_2)_n$ group having a straight or branched chain, B represents hydrogen, an alkoxy radical containing 1 to 3 carbon atoms or a group of the formula

(Formula 2)

in which $R_1$ and $R_2$ may independently be selected from the group consisting of methoxy, ethoxy, a lower alkyl or hydroxyalkyl radical containing 1 to 3 carbon atoms, whereby $R_1$ may also represent hydrogen, A is a 2-pyridyl radical, an unsubstituted phenyl radical or a phenyl radical substituted by at least one substituent in the ortho, meta and/or para position, E is selected from the group consisting of hydrogen, methyl, ethyl, propyl, butyl, hydroxyethyl, hydroxypropyl or hydroxybutyl and where the piperidine nucleus is attached at 2-, 3- or 4-position, or pharmaceutically acceptable thereof.

2. Process for preparing a compound according to claim 1, characterized in b) reacting a compound of the formula 3

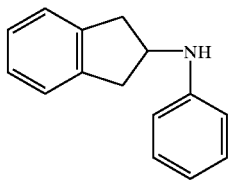

(Formula 3)

with a compound of the formula 4,

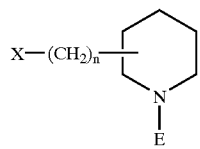

(Formula 4)

wherein E and n have the same meanings given in claim 1, except that E may not be hydrogen, and X is a reactive esterified hydroxy group, to form a compound of formula I; and b) hydrogenating a compound of the formula 1, wherein E is a residue removable by means of hydrogenolysis, to give a compound of formula 1 above, wherein E is hydrogen; and c) hydrolyzing a compound of the formula 1, wherein E is a residue removable by means of hydrolysis, to form a compound of formula 1, wherein E is hydrogen; and transforming free bases obtained into their salts or transforming salts obtained into their bases.

3. A process according to claim 2, wherein X is chloro, bromo or iodo.

4. A process according to claim 2, wherein reaction a) takes place in an inert organic solvent.

5. A process according to claim 2, wherein reaction a) takes place in the presence of a strong base.

6. A method of inducing local anesthesia in mammals, including man, comprising administration of a therapeutic amount of a compound of the general Formula 5

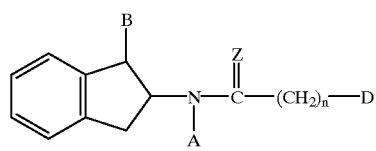

(Formula 5)

or an optically active isomer thereof, wherein n is equal to 1, 2, or 3, A represents an aromatic substituent, Z represents two hydrogen atoms or an oxygen atom, the $(CH_2)_n$ group having a straight or branched chain, B represents hydrogen, an alkoxy radical containing 1 to 3 carbon atoms or a group of the formula 6

(Formula 6)

in which $R_3$ and $R_4$ may independently be selected from the group consisting of methoxy, ethoxy, a lower alkyl or hydroxyalkyl radical containing 1 to 3 carbon atoms, whereby R may also represent hydrogen, A is a 2-pyridyl radical, an unsubstituted phenyl radical or a phenyl radical substituted by at least one substituent in the ortho, meta and/or para position, D represents a group of the formula 7

(Formula 7)

in which $R_1$ represents hydrogen, $R_2$ represents a lower alkyl or hydroxyalkyl radical containing 1 to 3 carbon atoms or a lower alkenyl or alkynyl radical containing 2 or 3 carbon atoms, or D may also represent a piperidine group, where the nitrogen substituent is selected from the group consisting of hydrogen, methyl, ethyl, propyl, butyl, hydroxyethyl, hydroxypropyl and hydroxybutyl and where the piperidine nucleus is attached at the 2-, 3- or 4-position.

7. The method of claim 6, wherein said local anesthesia is dermal anesthesia.

8. The method of claim 7 wherein said dermal anesthesia is induced in response to pain resulting from a member selected from the group consisting of surgical interventions, needle sticks, hemorrhoids, shingles, sunburn and insect bites.

9. The method of claim 6, wherein said local anesthesia is topical anesthesia of mucous membranes.

10. The method of claim 9 wherein said mucous membranes are selected from the group consisting of ocular, oral, otic, pharyngeal, tracheal, urogenital and rectal membranes.

11. The method of claim 6, wherein said local anesthesia is infiltration anesthesia.

12. The method of claim 6, wherein said local anesthesia is nerve blocks.

13. A pharmaceutical composition for induction of local anesthesia, containing as an active agent a local anesthetic inducing effective amount of at least one compound of the Formula 5

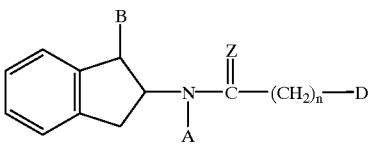

(Formula 5)

or an optically active isomer thereof, wherein n is equal to 1, 2, or 3, A represents an aromatic substituent, Z represents two hydrogen atoms or an oxygen atom, the $(CH_2)_n$ group having a straight or branched chain, B represents hydrogen, an alkoxy radical containing 1 to 3 carbon atoms or a group of the formula 6

(Formula 6)

in which $R_3$ and $R_4$ may independently be selected from the group consisting of methoxy, ethoxy, a lower alkyl or hydroxyalkyl radical containing 1 to 3 carbon atoms, whereby $R_3$ may also represent hydrogen, A is a 2-pyridyl radical, an unsubstituted phenyl radical or a phenyl radical substituted by at least one substituent in the ortho, meta and/or para position, D represents a group of the formula 7

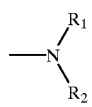

(Formula 7)

in which $R_1$ represents hydrogen, $R_2$ represents a lower alkyl or hydroxyalkyl radical containing 1 to 3 carbon atoms or a lower alkenyl or alkynyl radical containing 2 or 3 carbon atoms, or D may also represent a piperidine group, where the nitrogen substituent is selected from the group consisting of hydrogen, methyl, ethyl, propyl, butyl, hydroxyethyl, hydroxypropyl and hydroxybutyl and where the piperidine nucleus is attached at the 2-, 3- or 4-position.

14. The pharmaceutical composition of claim 13, wherein said local anesthesia is selected from the group consisting of dermal anesthesia, topical anesthesia, infiltration anesthesia and nerve blocks.

15. The pharmaceutical composition according to claim 13, wherein said local anesthesia is dermal anesthesia and wherein said compound comprises 0.5 to 10% by weight of the composition.

16. The pharmaceutical composition according to claim 13, wherein said local anesthesia is topical anesthesia and wherein the compound comprises 0.1 to 10% by weight of the composition.

17. The pharmaceutical composition according to claim 13, wherein said local anesthesia is infiltration anesthesia and wherein said compound comprises 0.1 to 5% by weight of the composition.

18. The pharmaceutical composition according to claim 13, wherein said local anesthesia is nerve blocks and wherein said compound comprises 0.1 to 5% by weight of the composition.

* * * * *